US 8,548,117 B2

(12) United States Patent
Noordhoek

(10) Patent No.: US 8,548,117 B2
(45) Date of Patent: Oct. 1, 2013

(54) SEMICIRCULAR INVERSED OFFSET SCANNING FOR ENLARGED FIELD OF VIEW 3D

(75) Inventor: Nicolaas Jan Noordhoek, Breda (NL)

(73) Assignee: Koninklijke Philips N.V., Eindhoven (NL)

( * ) Notice: Subject to any disclaimer, the term of this patent is extended or adjusted under 35 U.S.C. 154(b) by 151 days.

(21) Appl. No.: 13/139,329

(22) PCT Filed: Dec. 8, 2009

(86) PCT No.: PCT/IB2009/055572
§ 371 (c)(1),
(2), (4) Date: Jun. 13, 2011

(87) PCT Pub. No.: WO2010/070527
PCT Pub. Date: Jun. 24, 2010

(65) Prior Publication Data
US 2011/0255657 A1      Oct. 20, 2011

(30) Foreign Application Priority Data

Dec. 15, 2008 (EP) .................................... 08171597

(51) Int. Cl.
*A61B 6/03* (2006.01)
(52) U.S. Cl.
USPC .......................................................... 378/11
(58) Field of Classification Search
USPC .......................................... 378/4, 11, 19, 193
See application file for complete search history.

(56) References Cited

U.S. PATENT DOCUMENTS

| 5,848,117 | A | 12/1998 | Urchuk et al. |
| 7,372,939 | B2 | 5/2008 | Nabatame |
| 7,945,012 | B2 * | 5/2011 | Ye et al. ........................... 378/11 |
| 2004/0258195 | A1 | 12/2004 | Hara |
| 2005/0078785 | A1 * | 4/2005 | Endo ............................... 378/22 |
| 2005/0265523 | A1 | 12/2005 | Strobel |
| 2006/0039537 | A1 | 2/2006 | Strobel |

FOREIGN PATENT DOCUMENTS

| JP | 2006326319 A | 12/2006 |
| WO | 2008021671 A2 | 2/2008 |
| WO | 2010037911 A1 | 4/2010 |

* cited by examiner

Primary Examiner — Irakli Kiknadze

(57) ABSTRACT

A computed tomography acquisition method, an imaging system, a computer readable medium provides laterally displacing a radiation detector (204) from a position with centered detector geometry with a centered transverse field of view to a first offset position (212); emitting first radiation by the radiation source (202), detecting the first radiation by the radiation detector (204) and acquiring projection data indicative of the first radiation; rotating the support around the rotational axis (214) by 180°; emitting second radiation by the radiation source (202), detecting the second radiation by the radiation detector (204) and acquiring projection data indicative of the second radiation; displacing the radiation detector (204) from the first offset position to a second offset position (226), with opposite direction and double length of the first displacement (a); emitting third radiation by the radiation source (202), detecting the third radiation by the radiation detector (204) and acquiring projection data indicative of the third radiation; rotating the support around the rotational axis (214) by 180°; and emitting fourth radiation by the radiation source (202), detecting the fourth radiation by the radiation detector (204) and acquiring projection data indicative of the fourth radiation.

22 Claims, 3 Drawing Sheets

SEMICIRCULAR INVERSED OFFSET SCANNING FOR ENLARGED FIELD OF VIEW 3D

FIELD OF THE INVENTION

The present application relates to a method used in computed tomography (CT) and an X-ray CT apparatus. It finds particular application to x-ray CT for medical applications. It also finds application to article and security inspection, non-destructive testing, pre-clinical imaging, and other situations in which CT data can provide useful information about the structure or function of an object. Further, the present application relates to an imaging system, e.g. an X-ray imaging system, precisely a C-arm-system, a control device, configured to actuating means for displacing a radiation detector, a computer readable medium and a program element associated with said method.

BACKGROUND OF THE INVENTION

One area in which CT imaging systems have gained widespread acceptance is in medicine, where CT scanners are widely used by radiologists and other medical professionals in connection with the diagnosis and treatment of disease. The relatively recent adoption of multi-slice systems has further broadened the clinical application range of CT systems.

The data acquisition geometry of a conventional third generation x-ray CT system having a flat panel detector is shown in FIG. 1. FIG. 1 depicts a transaxial plane of a system, for example a central plane of a cone-beam system. An x-ray source 102 and an x-ray sensitive detector 104 are disposed on opposite sides of an examination region 106 and radially displaced from a center of rotation 114. A human patient, or other object to be examined 108 is supported in the examination region 106 by a suitable support 110. The source 102 emits radiation 112 which traverses the examination region 106 and is detected by the detector 104 as the source 102 and detector 104 rotate about a center of rotation 114.

In the illustrated full beam acquisition geometry, a central ray 116 of the x-ray beam 112 intersects the center of rotation 106 and is perpendicular to the detector transverse center 119. The detector transverse dimension 120 is such that the detector 104 detects radiation 112 which has traversed the entire transverse field of view (FOV) 118 at each projection angle. Thus, a complete angular sampling of the transverse FOV requires that data be collected over approximately 180° plus the x-ray beam 114 transverse fan angle. While illustrated in relation to a flat, panel detector, it will also be appreciated that the full beam acquisition geometry is applicable to systems in which the detector 104 is generally arcuate.

However, it is generally desirable to reduce the physical size of the detector required to achieve a given transverse FOV. For example, relatively larger detectors tend to be more complex and expensive to manufacture. Moreover, the size of the available detector arrays can be a limiting factor in the system design. These considerations become increasingly acute with the increasing popularity of multi-slice systems, and particularly as the relatively larger multi-slice detectors become a greater portion of the total system cost. In other words, in conventional 3D rotational x-ray systems, e.g. 3DRA, XperCT, CT scanners, portal imaging etc., the 3D reconstructed FOV is limited by the magnification and detector size of the detector (FOV=detector width/magnification). The magnification is the ratio between x-ray-focus-to-detector distance and x-ray-focus-to-isocenter distance. Typical values are 40 cm detector width, magnification 1.6×, thus 25 cm FOV in 3D. These systems typically scan over 180 degrees plus fan angle (~2*arc tan(0.5*detector width/"focal point-to-detector-distance"), typically 18 degrees fan angle.

Also, half beam acquisition geometry has been proposed. See, e.g., Gregor, et al., Conebeam X-ray Computed Tomography with an Offset Detector, IEEE 2003 (2003), Wang, et al., X-ray Micro-CT with a Displaced Detector Array, Med. Phys. 29 (7), July 2002; Lin, et al., Half Field of View Reduced-Size CT Detector, PCT publication WO 00/62647, dated 26 Oct. 2000.

Consequently, there remains room for improvement. For example, it is desirable to further improve the detector utilization while maintaining a suitable image quality. It is also desirable to simplify system construction.

Aspects of the present invention address these matters, and others.

SUMMARY OF THE INVENTION

In accordance with one aspect of the present invention, a computed tomography method using a radiation detector and a radiation source, both mounted on a support, the support rotatable around a rotational axis is proposed. The method comprises the following steps in alphabetic order:
 a) laterally displacing the radiation detector from a position with centered detector geometry with a centered transverse field of view to a first offset position;
 b) emitting first radiation by the radiation source, detecting the first radiation by the radiation detector and acquiring projection data indicative of the first radiation;
 c) rotating the support around the rotational axis by 180°;
 d) emitting second radiation by the radiation source, detecting the second radiation by the radiation detector and acquiring projection data indicative of the second radiation;
 e) laterally displacing the radiation detector from the first offset position to a second offset position, with opposite direction and double length of the first displacement (a);
 f) emitting third radiation by the radiation source, detecting the third radiation by the radiation detector and acquiring projection data indicative of the third radiation;
 g) rotating the support around the rotational axis by 180°;
 h) emitting fourth radiation by the radiation source, detecting the fourth radiation by the radiation detector and acquiring projection data indicative of the fourth radiation.

This solution increase the 3D field of view and introduces an offset of the detector with respect to the x-ray shadow of the isocentre. The detector is not placed centered, but shifted sideways by preferably less than half the detector width. If scans of 360 degrees are made with this system, an effective field of view can be reconstructed that is almost twice as large as that of a centered detector system. This is very desired, since e.g. a patients abdomen is typically larger than the typical said 25 cm FOV of a centered detector 3D scanner. The reconstruction of 360 degree+offset detector scanners, using the standard "modified Feldkamp technique", however is found to suffer from complications that are not present in the centered detector geometry. These complications can be explained in simple words as follows. To reconstruct the 3D volume well, it is necessary that opposing views (x-ray images taken from 180 degree differing direction), must match extremely well at their edges where the shadow of the isocentre falls. This requirement is very difficult to meet because x-ray scatter is different in the opposing views, and difficult to estimate accurately enough for correction, and because any geometrical inaccuracy (vibration, bending), that is not calibrated out, will be magnified many times as an artefact in the reconstruction.

Here, the invention presents a pragmatic solution for the said problems, preventing the mentioned complications in reconstruction and to a certain level even simplifying the construction of the system.

One idea of the invention is to use a positive detector offset and rotate over 180 degrees shift the detector (optionally focus too) to negative offset and finally rotate back over 180 degrees with a respective data acquirement after each shifting/rotating step, or with other words to implement a back and forward scanning system, that can shift the detector between 180 degree scans in a manner described in claim 1.

According to another aspect, the detector is a flat panel detector.

According to another aspect, the displacement takes place in a direction parallel to the detector plane.

According to another aspect, the detector includes a transition region in which the detector generate redundant projection data.

According to another aspect, the radiation source is shifted according to the displacement of the radiation detector.

According to another aspect, the rotational axis is the center of the transverse field of view.

According to another aspect, the source emits a radiation beam having a generally fan shaped transverse cross section, the cross section includes first and second outermost rays, and the outermost rays intersect the detector at different angles of incidence According to another aspect, a focal spot path from the source to the detector keeps a non-zero distance to the rotational axis during first, second, third, and forth emitting and detecting of radiation.

According to still another aspect, wherein the displacement distance from the position with centered detector geometry to the first position and to the second position is less than one half of the detector width in the direction of the displacement.

According to another aspect, the method used the opposing views to reconstruct a 3D imaging data volume.

According to yet another aspect, the computed tomography apparatus includes an x-ray source, an x-ray detector, and a reconstructor. The x-ray source is transversely displaced according to the method steps from and rotates about a center of rotation. The x-ray detector detects radiation emitted by the x-ray source and is transversely displaced from the center of rotation. The x-ray detector rotates about the center of rotation in a fixed mechanical relation to the x-ray source so as to acquire imaging data at a plurality of projection angles in the described manner. The x-ray source emits radiation having a transverse fan angle, and a complete angular sampling of a transverse field of view requires the acquisition of projection data over an angular range greater than 180° plus the fan angle. The reconstructor reconstructs the projection data to generate volumetric data indicative of the transverse field of view.

Further, in one embodiment an imaging system for acquiring projection images of a physical object is provided. The system comprises a radiation source that generates X-rays, a radiation detector for detecting rays of radiation originating from the radiation source and a support that rotatably supports the source and the detector around a rotational axis. The radiation detector is configured to be laterally displaced from a position with centered detector geometry with a centered transverse field of view (FOV) to a first offset position and from the first offset position to a second offset position. Preferably for imaging geometry back-calculation, carried out by a computer terminal the second displacement takes place in an opposite direction and with double length of the first displacement. Thus, the detector crosses its centered position during the second displacement.

In another aspect of the embodiment, the source is configured to be adjusted from a centered source position according to the detector displacement. The said source adjustment prevents radiation on regions which are not detected during detector offset positions.

According to yet another aspect a control device is prevented which is configured to actuating means for laterally displacing a radiation detector from a position with centered detector geometry with a centered transverse field of view to a first offset position and from the first offset position to a second offset position. Such means may include at least one motor drive and further a guide rail on each side of the preferably flat detector. The coupling between the detector and the motor drive may be carried out with at least one gear attached to a rotor of the motor drive and gear rod mounted on at least one side of the detector plane, wherein the gear and the gear rod are engaged with each other. With a control signal of a control device the detector may be displaced by the motor drive in every chosen intermediate position between two opposing offset end positions.

Further in one aspect a computer readable medium having stored thereon computer-executable instructions enabling a computer to carry out a method using a radiation detector and a radiation source, both mounted on a support, the support rotatable around a rotational axis, the method comprising steps mentioned for the method.

According to vet another aspect, a computer program element configured and arranged to control when executed on a computer a method using a radiation detector and a radiation source, both mounted on a support, the support rotatable around a rotational axis, the method comprising steps in the following order: displacing the radiation detector from a position with centered detector geometry with a centered transverse field of view to a first offset position, emitting first radiation by the radiation source, detecting the first radiation by the radiation detector and acquiring projection data indicative of the first radiation, rotating the support around the rotational axis by 180°, emitting second radiation by the radiation source, detecting the second radiation by the radiation detector and acquiring projection data indicative of the second radiation, displacing the radiation detector from the first offset position to a second offset position, with opposite direction and double length of the first displacement, emitting third radiation by the radiation source, detecting the third radiation by the radiation detector and acquiring projection data indicative of the third radiation, rotating the support around the rotational axis by 180°, and emitting fourth radiation by the radiation source, detecting the fourth radiation by the radiation detector and acquiring projection data indicative of the fourth radiation.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
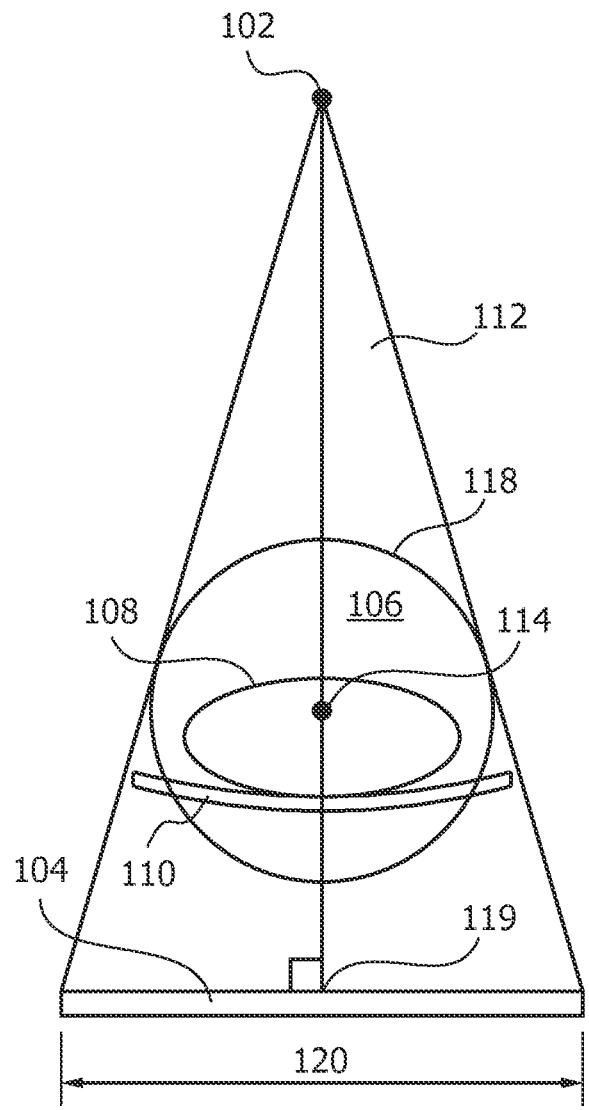
FIG. 1 shows a transaxial view of a prior art full beam CT acquisition geometry.
Figure 2:
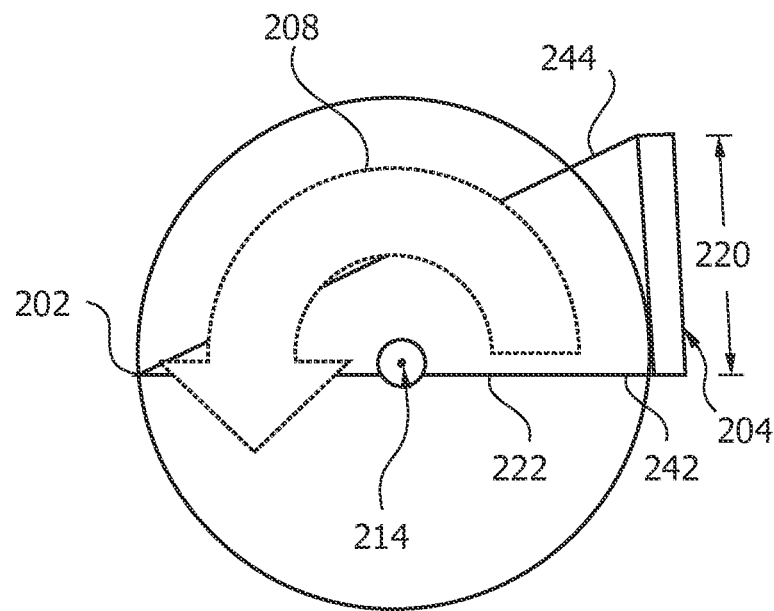
FIG. 2 shows an according to the invention with detector in a first offset position.
Figure 4:
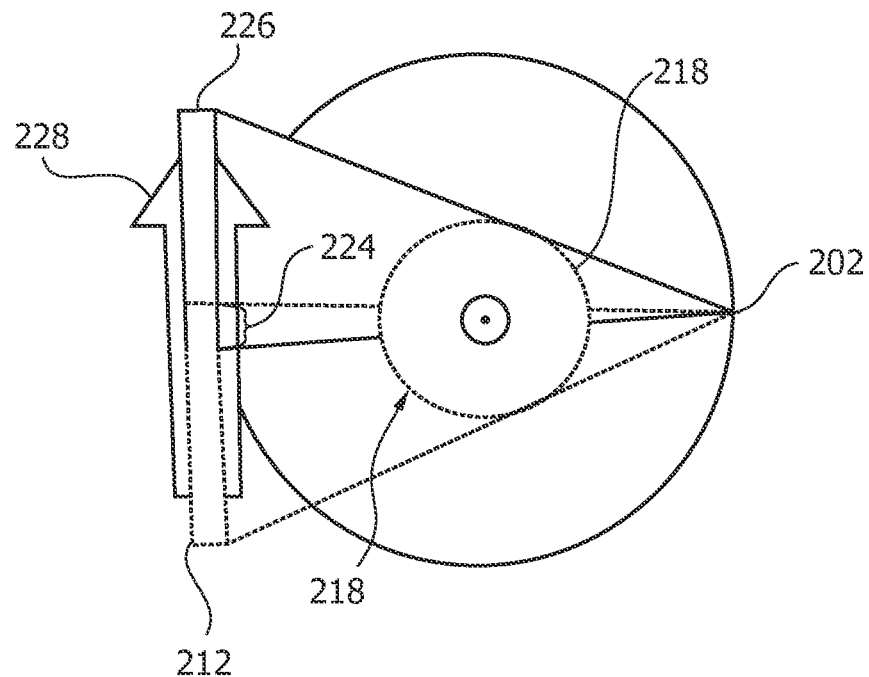
FIG. 4 shows the acquisition geometry of FIG. 3 after detector shifting to a second offset position.

Relative to a full beam geometry, the detector 204 of an imaging system shown in FIG. 2 is shifted in a transverse direction by approximately one-half its transverse dimension or width 120. A ray or projection 222 with a small distance to the center of rotation 214 is perpendicular to the plane of the detector 204. At a given projection angle, the detector 204 detects radiation which has traversed approximately one-half the transverse FOV 218 shown in FIG. 4 (note that an overlap or transition region 224 ensures that projection data is acquired at a central region of the transverse FOV 218). While the half beam acquisition geometry achieves a relatively larger transverse FOV relative to the full beam geometry shown in the embodiment of FIG. 1, complete angular sampling of the transverse FOV requires that data be collected over an angular range of approximately 360°. The computed tomography method uses a X-radiation source 202, mounted with the detector 204 on a support not shown here. The source (202) emits a radiation beam having a generally fan shaped transverse cross section, the cross section includes first and second outermost rays 242, 244, and the outermost rays intersect the detector at different angles of incidence. The support is rotatable around the rotational axis 214. In a first step a) a laterally displacing of the radiation detector from a position with centered detector geometry with a centered transverse field of view to a first offset position 212 shown in FIG. 2 takes place. After emitting first radiation by the radiation source 202 detecting the first radiation by the radiation detector and acquiring projection data indicative of the first radiation a rotating of the support around the rotational axis by 180° takes place in step c) indicated by arrow 208.

Figure 3:
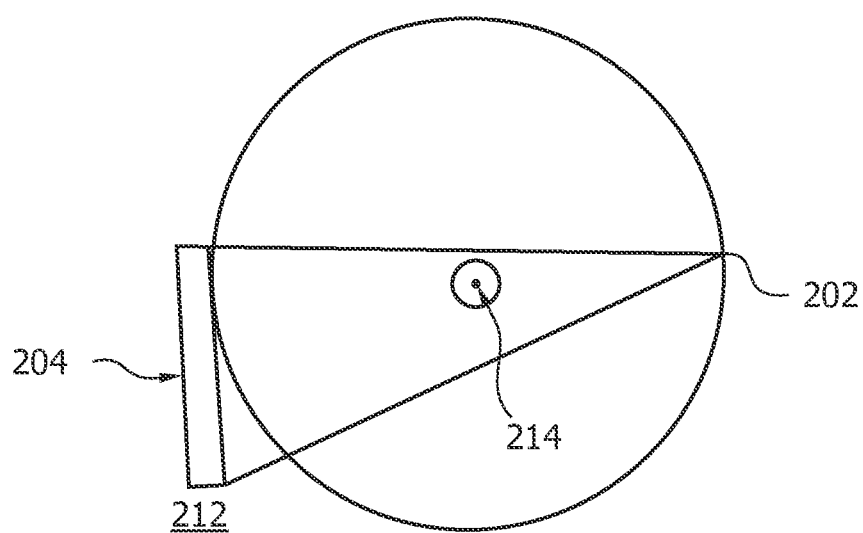
FIG. 3 shows the acquisition geometry of FIG. 2 after a first 180 degree rotation.
Figure 5:
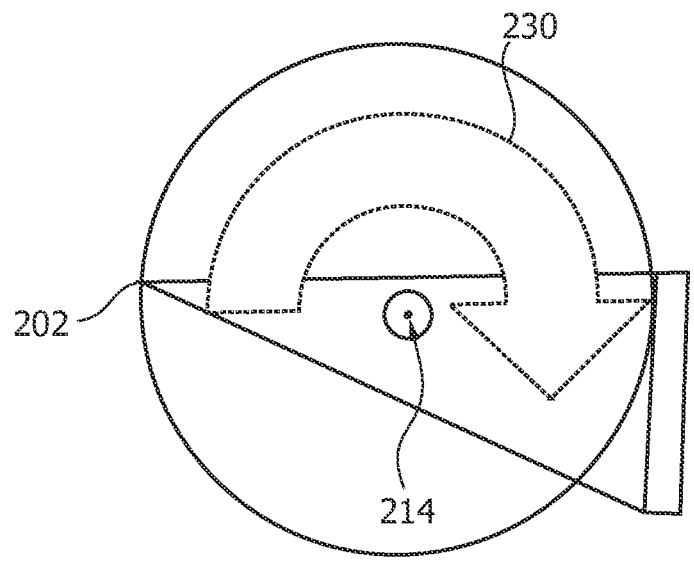
FIG. 5 shows the acquisition geometry of FIG. 4 after a second 180 degree rotation.

After rotating to the position shown in FIG. 3 in step d), the emitting of a second radiation by the radiation source 202 of the imaging system, detecting the second radiation by the radiation detector 204 and acquiring projection data indicative of the second radiation takes place in the fourth step d). Further in step e) shown in FIG. 4, the detector will be displaced (arrow 228) from the first offset position 212 to a second offset position 226 (solid line) in plane detector direction, with opposite direction and double length of the first displacement (step a)). After emitting third radiation by the radiation source, detecting the third radiation by the radiation detector and acquiring projection data indicative of the third radiation in the next step, a further rotating of the support around the rotational axis 214 by 180° takes place, indicated by arrow 230 in FIG. 5. In the position of FIG. 5 emitting fourth radiation by the radiation source, detecting the fourth radiation by the radiation detector and acquiring projection data indicative of the fourth radiation takes finally place to complete the data for one rotation angle.

The FIGS. 2 to 5 show An improved, double displaced CT acquisition geometry in which both the source and detector are displaced from the imaging isocenter. It is clear for the skilled person that a displacement of the detector alone is also possible, without leaving the scope of the invention.

While the foregoing has focused on x-ray CT system in which the source 202 is the focal spot of an x-ray tube and hence substantially a point source, other alternatives are contemplated. For example, the source 202 may be implemented as a line source. Wedge and other beam geometries are also contemplated. Gamma and other radiation sources may also be used. Multiple sources 202 and detectors 204 may also be provided, in which case corresponding sets of sources and detectors may be offset angularly and/or longitudinally from one another. Note that in systems having multiple angularly offset sources and detectors, the rotation required to provide a complete angular sampling range is ordinarily reduced compared to systems having a single source detector pair, and the trajectory may be adjusted accordingly.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computed tomography method using a radiation detector and a radiation source, both mounted on a support, the support rotatable around a rotational axis; the method comprising: a) creating a first displacement by laterally displacing the radiation detector from a position with centered detector geometry with a centered transverse field of view to a first offset position, said detector being at a first rotational orientation with respect to said axis; b) with said detector at said first orientation, emitting first radiation by the radiation source, and detecting the first radiation by the radiation detector; and acquiring projection data indicative of the first radiation; c) halting the emitting of the first radiation, and transitioning to a second rotational orientation of said radiation detector by rotating the support around the rotational axis by 180°; d) at said second rotational orientation, emitting second radiation by the radiation source, and detecting the second radiation by the radiation detector; and acquiring projection data indicative of the second radiation; e) laterally displacing the radiation detector from the first offset position to a second offset position, with opposite direction and double length of the first displacement and so as to assume a third rotational orientation of said radiation detector; f) at said third rotational orientation, emitting third radiation by the radiation source, and detecting the third radiation by the radiation detector; and acquiring projection data indicative of the third radiation; g) halting the emitting of the third radiation, and transitioning to a fourth rotational orientation of said detector by rotating the support around the rotational axis by 180°; h) at said fourth rotational orientation emitting fourth radiation by the radiation source, and detecting the fourth radiation by the radiation detector; and acquiring projection data indicative of the fourth radiation.

2. The method of claim 1, wherein the detector is a flat panel detector.

3. The method of claim 1, wherein the displacement takes place in a direction parallel to the detector plane.

4. The method according to claim 1, wherein the detector includes a transition region in which the detector generate redundant projection data.

5. The method according to claim 1, wherein the rotational axis is the center of the transverse field of view.

6. The method according to claim 1, wherein the source emits a radiation beam having a generally fan shaped transverse cross section, the cross section includes first and second outermost rays, and the outermost rays intersect the detector at different angles of incidence.

7. The method according to claim 1, wherein a focal spot path from the source to the detector keeps a non-zero distance to the rotational axis during first, second, third, and fourth emitting and detecting of radiation.

8. The method according to claim 1, wherein the displacement distance from the position with centered detector geometry to the first position and to the second position is less than one half of the detector width in the direction of the displacement.

9. The method according to claim 1, comprising the step using opposing views to reconstruct a 3D imaging data volume.

10. The imaging system of claim 1, wherein the source is configured to be adjusted from a centered source position according to the detector displacement.

11. A computed tomography method using a radiation detector and a radiation source, both mounted on a support, the support rotatable around a rotational axis; the method comprising:
  a) laterally displacing the radiation detector from a position with centered detector geometry with a centered transverse field of view to a first offset position;
  b) emitting first radiation by the radiation source, detecting the first radiation by the radiation detector and acquiring projection data indicative of the first radiation;
  c) rotating the support around the rotational axis by 180°;
  d) emitting second radiation by the radiation source, detecting the second radiation by the radiation detector and acquiring projection data indicative of the second radiation;
  e) laterally displacing the radiation detector from the first offset position to a second offset position, with opposite direction and double length of the first displacement (a);
  f) emitting third radiation by the radiation source, detecting the third radiation by the radiation detector and acquiring projection data indicative of the third radiation;
  g) rotating the support around the rotational axis by 180°;
  h) emitting fourth radiation by the radiation source, detecting the fourth radiation by the radiation detector and acquiring projection data indicative of the fourth radiation,
  wherein the radiation source is shifted according to the displacement of the radiation detector.

12. A computed tomography imaging system comprising a radiation detector and a control device, said device configured with an actuator for creating a first displacement by laterally displacing said detector from a position with centered detector geometry with a centered transverse field of view (FOV) to a first offset position and from the first offset position to a second offset position, with opposite direction and double length of the first displacement, said system configured such that: said first offset position exists at a first rotational orientation, and at a second rotational orientation, of said detector with respect to an axis of rotation of said detector, imaging acquisition being performed at both orientations; and said second offset position exists at a third rotational orientation of said detector with respect to said axis, imaging acquisition resuming upon reaching said second rotational orientation which is attained after said first rotational orientation.

13. The imaging system of claim 12, the first and second rotational orientations being separated by 180°.

14. The imaging system of claim 12, said system configured for acquiring projection images of a physical object and comprising a radiation source that generates X-rays, said detector configured for detecting rays of radiation originating from said radiation source, said system further comprising a support that rotatably supports said source and said detector around said axis.

15. The imaging system of claim 12, each of the first, second and third rotational orientations being definable in relation to a fixed point on said detector.

16. A non-transitory computer readable medium having stored thereon computer-executable instructions enabling a computer to carry out a method of enlarging field of view using a radiation detector and a radiation source, both mounted on a support, the support rotatable around a rotational axis; the method comprising steps in the following order: a) creating a first displacement by laterally displacing the radiation detector from a position with centered detector geometry with a centered transverse field of view to a first offset position; b) emitting first radiation by the radiation source, detecting the first radiation by the radiation detector and acquiring projection data indicative of the first radiation; c) rotating the support around the rotational axis by 180°; d) emitting second radiation by the radiation source, detecting the second radiation by the radiation detector and acquiring projection data indicative of the second radiation; e) laterally displacing the radiation detector from the first offset position to a second offset position, with opposite direction and double length of the first displacement; f) emitting third radiation by the radiation source, detecting the third radiation by the radiation detector and acquiring projection data indicative of the third radiation; g) rotating the support around the rotational axis by 180°; h) emitting fourth radiation by the radiation source, detecting the fourth radiation by the radiation detector and acquiring projection data indicative of the fourth radiation, none of said steps involving acquisition of projection data via said detector while said support moves rotationally with respect to said axis.

17. A computed tomography imaging system comprising a radiation source, a radiation detector and a control device, said device configured with an actuator for creating a first displacement by laterally displacing said detector from a position with centered detector geometry with a centered transverse field of view (FOV) to a first offset position and from said first offset position to a second offset position, said system being configured for performing a plurality of acts, said plurality comprising the act of:
  for image reconstruction of a three-dimensional imaging data volume, acquiring projection data over an angular range, rotation angle by rotation angle, said acquiring for a rotation angle comprising a plurality of steps, said plurality comprising steps a) through g) in the following relative order: a) imaging, via said detector, with said first displacement, b) performing a first rotation of said detector, c) imaging via said detector; d) performing a second displacement of said detector in a direction opposite to that of said first displacement; e) imaging via said detector; f) performing a second rotation in a direction opposite to that of said first rotation; and g) imaging via said detector,
  said system being further configured for, in performing said reconstruction, relying, for projection data, on the rotation-angle-specific imaging in the steps a), c), e) and g).

18. The system of claim 17, configured for said relying without need for imaging, via said detector, between said steps a), c), e) and g).

19. The system of claim 17, step d) comprising displacing a focus of an imaging beam incident on said detector according to said second displacement.

20. The system of claim 17, said first displacement being in a direction that tangentially corresponds to the direction of said first rotation.

21. The system of claim 17, configured not to acquire image data via said detector during said steps a), c), e) and g).

22. The system of claim 17, the first and second rotations each being 180°.

* * * * *